(12) United States Patent
Hughes et al.

(10) Patent No.: US 7,410,934 B2
(45) Date of Patent: *Aug. 12, 2008

(54) AQUEOUS VISCOELASTIC FLUID

(75) Inventors: Trevor Hughes, Cambridge (GB); Timothy Gareth John Jones, Cottenham (GB); Gary John Tustin, Sawston (GB); Jian Zhou, Sugar Land, TX (US)

(73) Assignee: Schlumberger Technology Corporation, Ridgefield, CT (US)

( * ) Notice: Subject to any disclaimer, the term of this patent is extended or adjusted under 35 U.S.C. 154(b) by 295 days.

This patent is subject to a terminal disclaimer.

(21) Appl. No.: 10/250,416

(22) PCT Filed: Feb. 13, 2002

(86) PCT No.: PCT/GB02/00606

§ 371 (c)(1),
(2), (4) Date: Dec. 11, 2003

(87) PCT Pub. No.: WO02/064947

PCT Pub. Date: Aug. 22, 2002

(65) Prior Publication Data

US 2004/0094301 A1    May 20, 2004

(30) Foreign Application Priority Data

Feb. 13, 2001  (GB) .................................. 0103449.5

(51) Int. Cl.
*C09K 8/584* (2006.01)
*C09K 8/68* (2006.01)
*E21B 43/22* (2006.01)
*E21B 43/27* (2006.01)

(52) U.S. Cl. .................. 507/239; 507/248; 507/260; 507/265; 507/266; 507/267; 166/271; 166/308.2

(58) Field of Classification Search .............. 507/129, 507/239, 248, 260
See application file for complete search history.

(56) References Cited

U.S. PATENT DOCUMENTS 3,762,932 A * 10/1973 Buddemeyer et al. ....... 426/554

(Continued)

FOREIGN PATENT DOCUMENTS

EP    0 835 983 A2    4/1998

(Continued)

OTHER PUBLICATIONS

Raghavan, S.R. and Kaler, E.R., "Highly Viscoelastic Wormlike Micellar Solutions Formed by Cationic Surfactants with Long Unsaturated Tails", Langmuir 17 (2001) 300-306, published on Web Dec. 16, 2000 by ACS.*
G.C. Maitland: "Oil and Gas Production", Current Opinion in Colloid & Interface Science, 5 (2000) 301-311.*
Butler et al The hydrolysis of acetic anhydride. Part VII. Catalysis by pyridine and methylpyridines in acetate buffers Journal of the Chem. Society, 1961, pp. 4362-4367.

(Continued)

*Primary Examiner*—Randy Gulakowski
*Assistant Examiner*—John J Figueroa
(74) *Attorney, Agent, or Firm*—Steven Gahlings, Esq.; James McAleenan, Esq.; Jody Lynn DeStefansi, Esq.

(57) ABSTRACT

The invention concerns an aqueous viscoelastic fluid for use in the recovery of hydrocarbons. According to the invention, the aqueous viscoelastic fluid comprises a monomer, a dimer or an oligomer of a viscoelastic surfactant able to form a viscoelastic gel under downhole conditions, said surfactant comprising a hydrophobic tail and a hydrophilic head, and being of the following formulae: R—X—Y-Z where R is the hydrophobic tail of the surfactant, Z is the hydrophilic head of the surfactant, said hydrophilic head being charged, X is a stabilising group and Y chain is a linear, saturated or unsaturated, hydrocarbon chain of 1, 2 or 3 carbon atoms or a branched, saturated or unsaturated hydrocarbon chain wherein the main chain is of 1, 2 or 3 carbon atoms, possibly incorporating an aromatic ring.

13 Claims, 6 Drawing Sheets

U.S. PATENT DOCUMENTS

| | | | |
|---|---|---|---|
| 4,806,256 A * | 2/1989 | Rose et al. | 252/71 |
| 4,853,138 A * | 8/1989 | Loza et al. | 507/211 |
| 5,231,224 A * | 7/1993 | Gerdau et al. | 510/494 |
| 5,258,137 A | 11/1993 | Bonekamp et al. | |
| 5,466,396 A * | 11/1995 | Madison et al. | 510/153 |
| 5,551,516 A * | 9/1996 | Norman et al. | 166/308.2 |
| 5,922,663 A * | 7/1999 | Gabriel et al. | 510/299 |
| 5,964,295 A | 10/1999 | Brown et al. | |
| 5,979,555 A * | 11/1999 | Gadberry et al. | 166/270.1 |
| 5,979,557 A | 11/1999 | Card et al. | |
| 6,239,183 B1 * | 5/2001 | Farmer et al. | 516/102 |
| 6,306,800 B1 | 10/2001 | Samuel et al. | |
| 6,412,561 B1 | 7/2002 | Brown et al. | |
| 6,433,075 B1 * | 8/2002 | Davies et al. | 524/815 |
| 6,435,277 B1 | 8/2002 | Qu et al. | |
| 6,455,483 B1 * | 9/2002 | Carey | 510/247 |
| 6,767,869 B2 * | 7/2004 | DiLullo et al. | 507/244 |
| 2002/0004464 A1 | 1/2002 | Nelson et al. | |

FOREIGN PATENT DOCUMENTS

| | | |
|---|---|---|
| EP | 0 835 983 A3 | 4/1998 |
| GB | 2 334 277 A | 8/1999 |
| WO | 94/09852 A1 | 5/1994 |
| WO | 98/56497 A1 | 12/1998 |
| WO | 01/18147 A1 | 3/2001 |
| WO | 01/77487 A2 | 10/2001 |
| WO | 01/77487 A3 | 10/2001 |

OTHER PUBLICATIONS

Fersht et al The acetylpyridinium ion intermediate in pyridine-catalyzed hydrolysis and acyl transfer reactions of acetic anhydride. Observation, kinetics, structure-reactivity correlations, and effects of concentrated salt solutions Journal of the American Chemical Society, vol. 92, 1970, pp. 5432-5442.

Holmberg Cleavable surfactants Novel Surfactants (Holmberg ed.), Marcel Dekker Inc, New York, 1998, pp. 333-358.

Kaiser et al Synthesis of esters of acid-unstable alcohols by means of n-butyllithium Journal of Organic Chemistry, vol. 35, No. 4, 1970, pp. 1198-1199.

Kivinen Mechanisms of substitution at the COX group The Chemistry of Acyl Halides (Patai ed.), Interscience Publishers, New York, 1972, pp. 177-230.

Krüger et al Esterquats Novel Surfactants (Holmberg ed.), Marcel Dekker Inc, New York, 1998, pp. 115-138.

Satchell An outline of acylation Quarterly Reviews of the Chem. Society, vol. 17, 1963, pp. 160-203.

Smith et al Aliphatic nucleophilic substitution March's Advanced Organic Chemistry, $5^{th}$ edition, Wiley-Interscience, New York, 2001, pp. 498-502, 506-514, 574-578.

Smith et al Aromatic electrophilic substitution March's Advanced Organic Chemistry, $5^{th}$ edition, Wiley-Interscience, New York, 2001, pp. 701-704.

Sommer et al Alkylation of amines. A general exhaustive alkylation method for the synthesis of quaternary ammonium compounds Journal of Organic Chemistry, vol. 36, No. 6, 1971, pp. 824-828.

Sommer et al Alkylation of amines. A new method for the synthesis of quaternary ammonium compounds from primary and secondary amines Journal of Organic Chemistry, vol. 35, 1970, pp. 1558-1562.

Yoneda et al A kinetic study of the reaction between sulfite ion and propylene oxide Journal of Organic Chemistry, vol. 40, No. 3, 1975, pp. 375-377.

\* cited by examiner

AQUEOUS VISCOELASTIC FLUID

The present invention concerns an aqueous viscoelastic fluid for use in the recovery of hydrocarbons and, in particular, for use as a fracturing fluid.

BACKGROUND OF THE INVENTION

Hydrocarbons such as oil or natural gas are obtained from hydrocarbon-bearing subterranean geologic formations via flow paths connecting a reservoir of said formations and the wellbore. Impeded flow paths may lead to an inadequate hydrocarbon production. In such case, various techniques are used to stimulate this production. Amongst these techniques, it is common to inject specialised fluids via the wellbore into the formation at sufficient pressures to create fractures in the formation rocks through which the hydrocarbons may more readily flow into the wellbore. The latter technique is referred to as fracturing or hydraulic fracturing and the specialised fluids used in said technique are referred to as fracturing fluids.

Ideally, fracturing fluids should impart a minimal pressure drop in the pipe within the wellbore during placement and have an adequate viscosity to carry a propping agent that prevents the fracture from closing. Also, they should have a minimal leak-off rate and should degrade so as not to leave residual material that may impede the flow of hydrocarbons into the wellbore.

PRIOR ART

Aqueous fracturing fluids wherein the gelling agent is a viscoelastic surfactant have been developed and commercialised. They are disclosed notably in the patents published under the numbers U.S. Pat. No. 4,695,389, U.S. Pat. No. 4,725,372 and U.S. Pat. No. 5,551,516. An example of such fluid is commercialised by the company group Schlumberger™ under the trademark ClearFRAC™. It is a mixture of a quaternary ammonium salt, erucyl-N,N-bis(2-hydroxyethyl)-N-methyl ammonium chloride, with isopropanol and brine, said brine typically including water and either 3% by weight of ammonium chloride or 4% by weight of potassium chloride. In viscoelastic surfactant based fluids, surfactant molecules, present at a sufficient concentration, aggregate into overlapping worm- or rod-like micelles. This confers a sufficient viscoelasticity to the fluids for carrying the propping agent. At very high shear rate however, in particular above $170 s^{-1}$, the viscosity falls drastically. This allows the fluid to be pumped down the wellbore. Also, the worm- or rod-like micellar aggregates tend to break by contact with hydrocarbons and, if no surfactant emulsion is effectively formed, the surfactant molecules are normally carried along the fracture to the well bore during hydrocarbon backflow.

Erucyl-N,N-bis(2-hydroxyethyl)-N-methyl ammonium chloride is normally able to form stable gels at temperatures up to about 180° F. (82° C.). Above this temperature, the gel degrades and it is not possible to use this quaternary ammonium salt for fracturing application without adding gel stabilizers, such as salicylate. Nevertheless, even in the presence of salicylate, the gel degrades at temperatures of about 240° F. (116° C.).

More stable viscoelastic gels have been developed. For example, they are based on an erucyl betaine surfactant. Such gels degrade at temperatures above 200° F. (93.33° C.).

However, the temperature range for which fracturing fluids are required is 80 to 400° F. (27 to 204° C.). There is therefore a need for aqueous viscoelastic surfactant fluids able to form gels resistant to temperatures in the range 270 (132) to about 400° F. (204° C.). It would be particularly beneficial to have a set of viscoelastic surfactant fluids, each of said viscoelastic surfactant fluids stable at a given temperature range above 200° F., all temperature ranges being complementary one to another to cover all temperatures between 200 (93) and 400° F. (204° C.)

SUMMARY OF THE INVENTION

Considering the above prior art, one problem that the invention is proposing to solve is the formulation of an aqueous viscoelastic fluid for use in the recovery of hydrocarbons and, in particular, for use as a fracturing fluid, said fluid being able to form a gel resistant to high temperatures.

As a solution to the above problem, the invention concerns, in a first aspect, an aqueous viscoelastic fluid for use in the recovery of hydrocarbons, comprising a monomer, a dimer or an oligomer of a viscoelastic surfactant able to form a viscoelastic gel under downhole conditions, said surfactant comprising a hydrophobic tail and a hydrophilic head, and being of the following formulae:

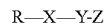

where R is the hydrophobic tail of the surfactant, Z is the hydrophilic head of the surfactant, said hydrophilic head being charged, X is a stabilising group and Y is a linear, saturated or unsaturated, hydrocarbon chain of 1, 2 or 3 carbon atoms or a branched, saturated or unsaturated hydrocarbon chain wherein the main chain is of 1, 2 or 3 carbon atoms, possibly incorporating an aromatic ring.

In a second aspect, the invention concerns a method for use in the recovery of hydrocarbons comprising the following steps: providing an aqueous viscoelastic surfactant fluid comprising a monomer, a diner or an oligomer of a viscoelastic surfactant able to form a viscoelastic gel under downhole conditions, said surfactant comprising a hydrophobic tail and a hydrophilic head, and being of the following formulae:

where R is the hydrophobic tail of the surfactant, Z is the hydrophilic head of the surfactant, said hydrophilic head being charged, X is a stabilising group and Y is a linear, saturated or unsaturated, hydrocarbon chain of 1, 2 or 3 carbon atoms or a branched, saturated or unsaturated hydrocarbon chain wherein the main chain is of 1, 2 or 3 carbon atoms, possibly incorporating an aromatic ring.

As defined by the above formulae, the fluid is able to form a gel at high temperatures, practically above about 200° F. (93° C.). Such fluid may be then used for hydrocarbon recovery and, in particular, for fracturing application, at downhole locations where the average temperature exceeds 200° F. (93° C.).

BRIEF DESCRIPTION OF THE DRAWINGS

The invention will be better understood in the light of the following description of non-limiting and illustrative embodiments given with reference to the accompanying drawings, in which:

the FIG. 1 shows the structure of the oleyl amide 2-methylsuccinate anion;

Figure 1:
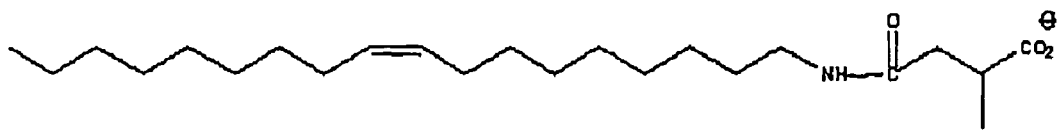
Figure 2:
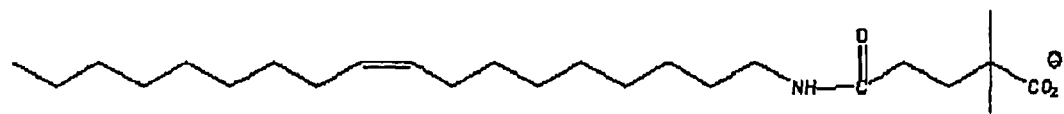
Figure 3:
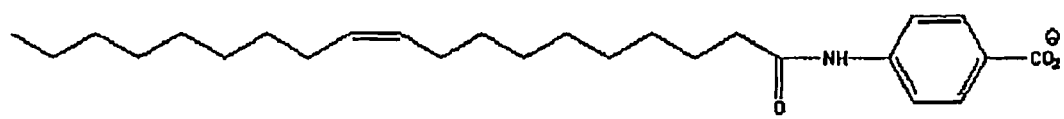
Figure 4:
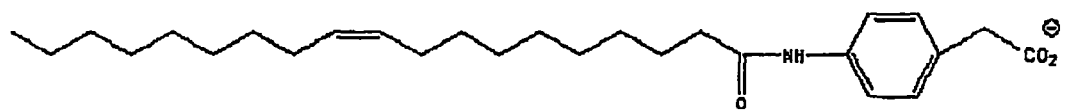
Figure 5:
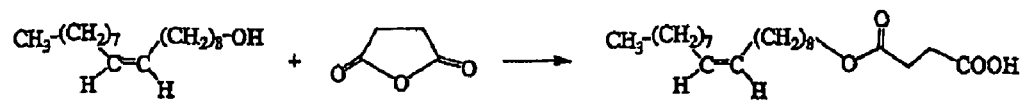
Figure 6:
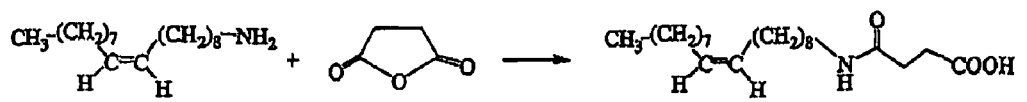
Figure 7:
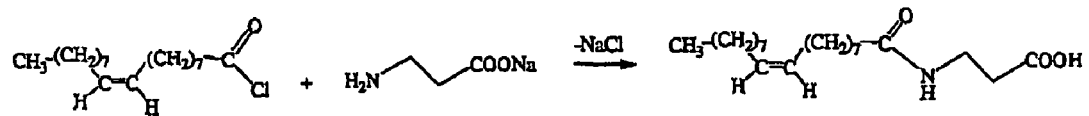
Figure 8:
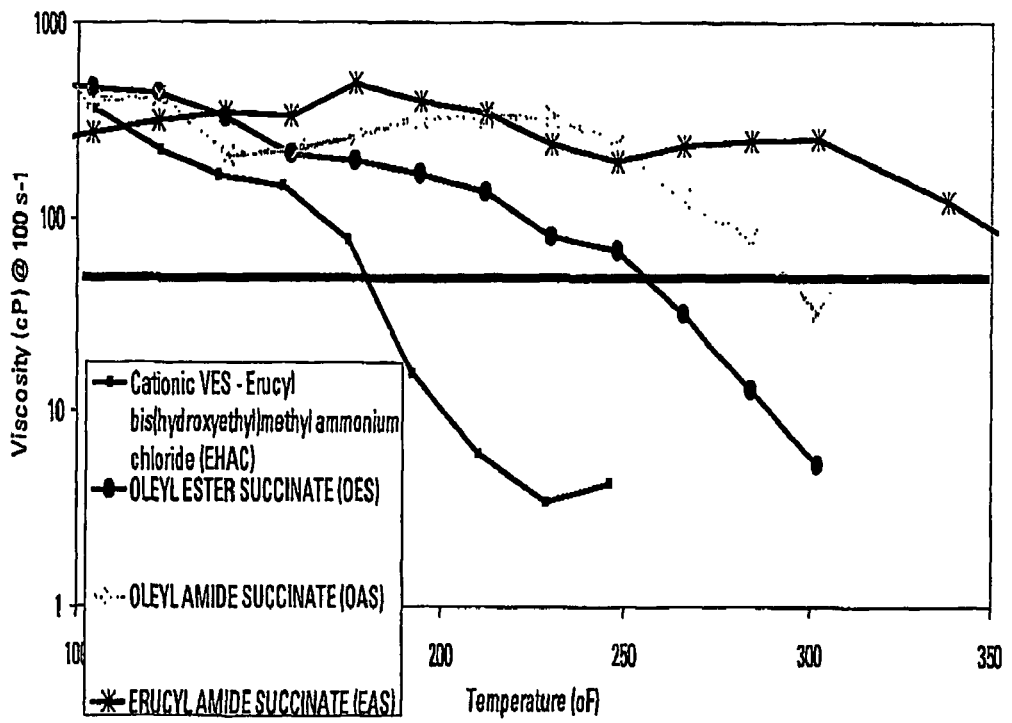
Figure 9:
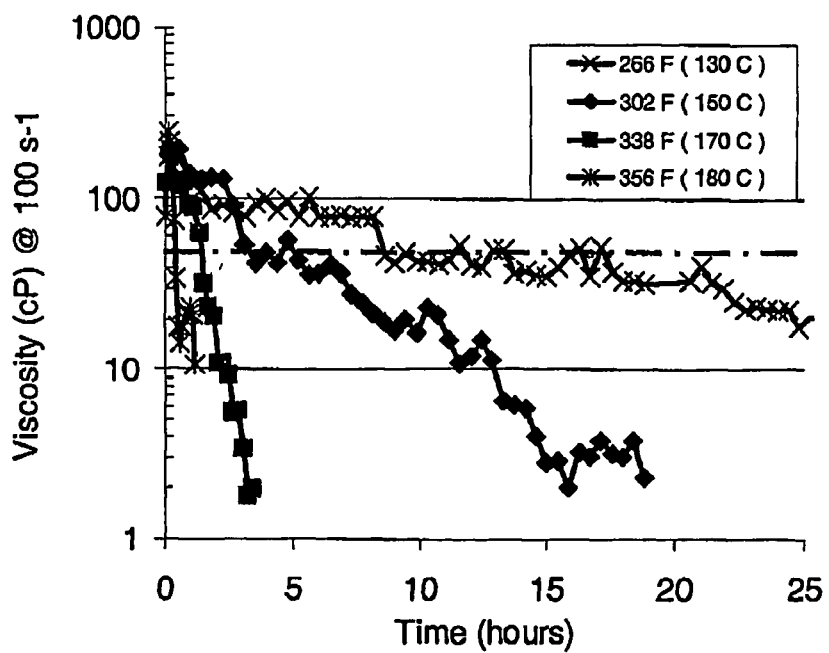
Figure 10:
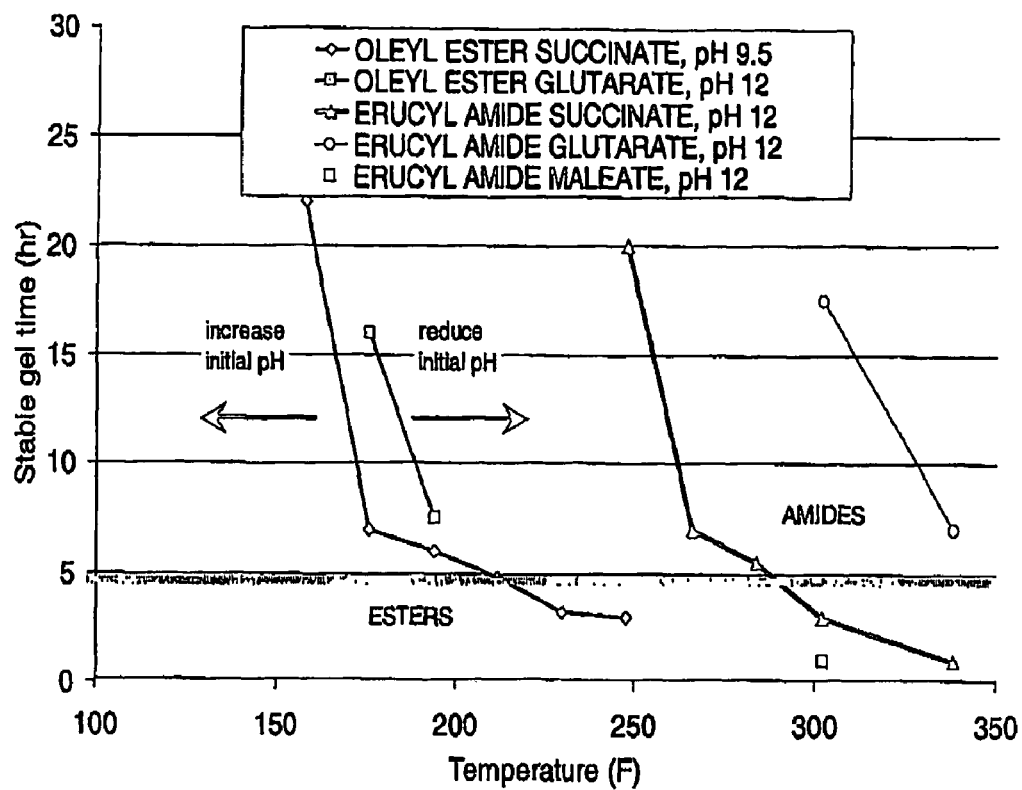
Figure 11:
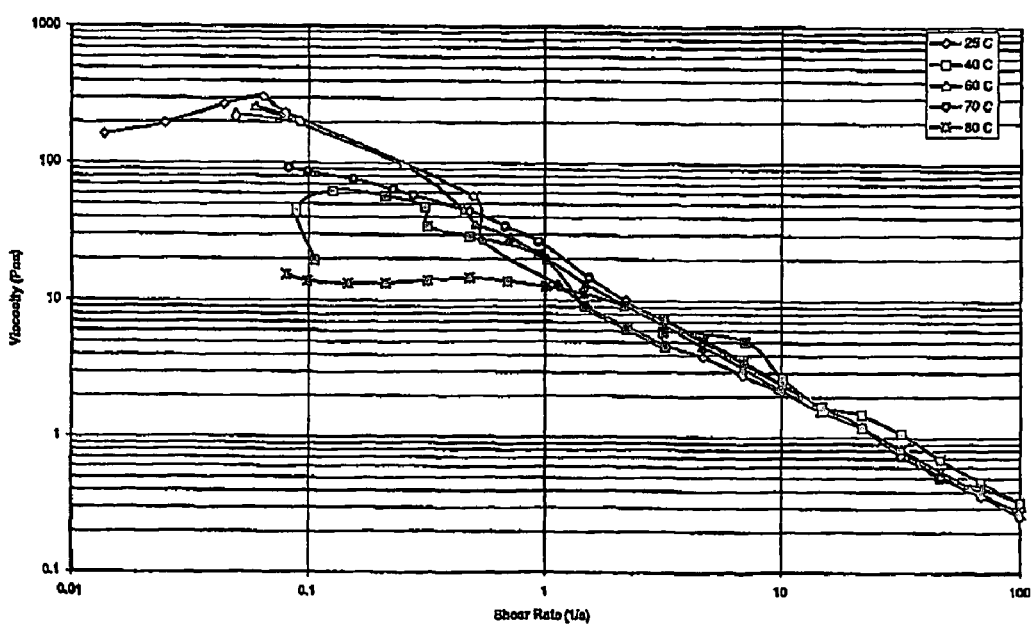
Figure 12:
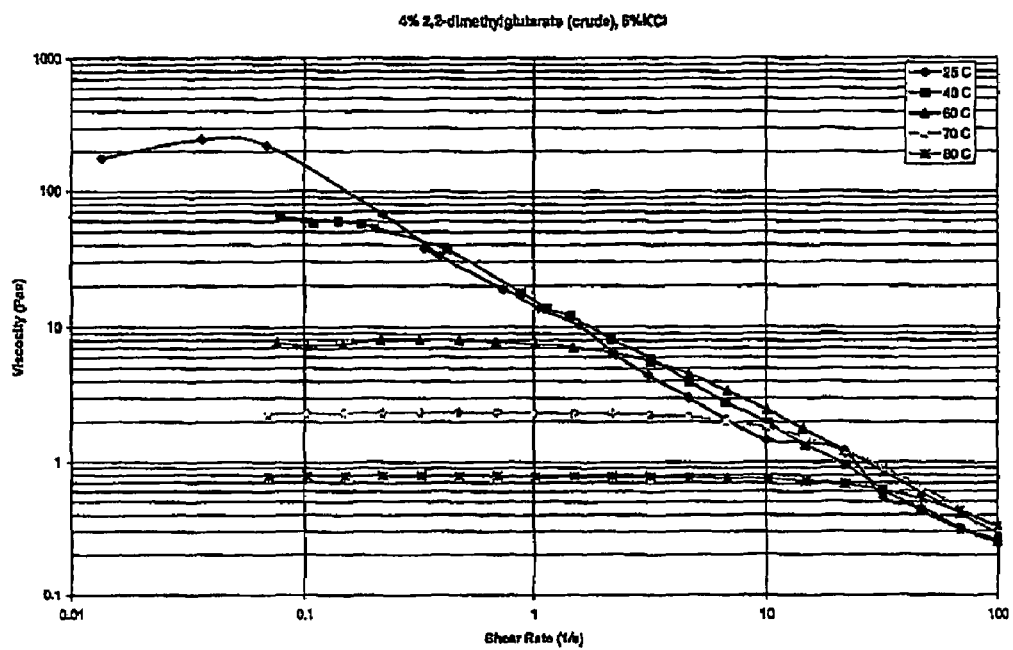
Figure 13:
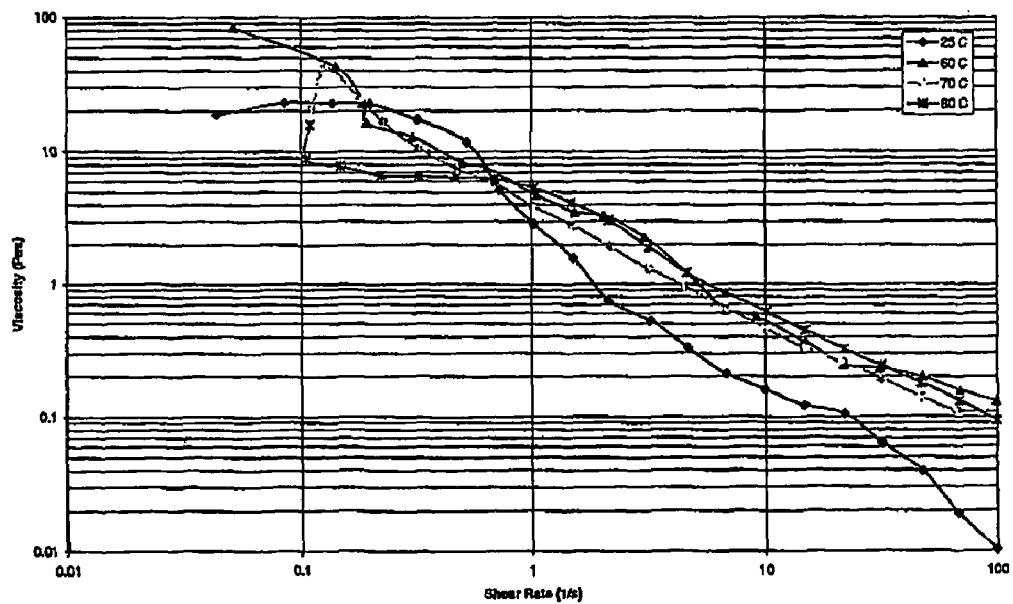
Figure 14:
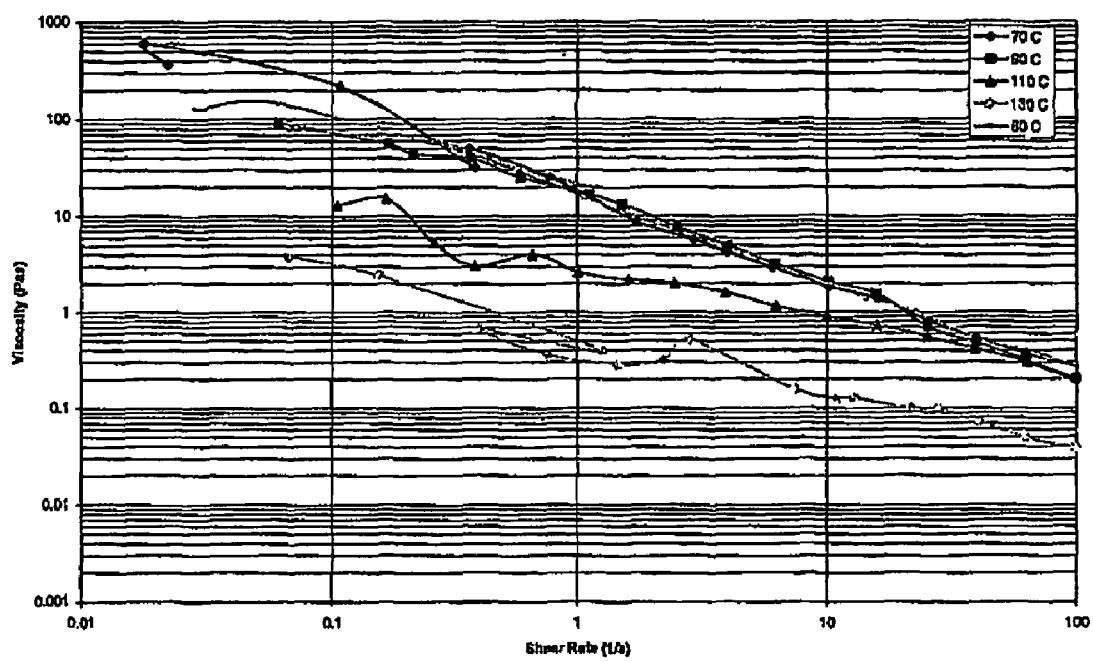

the FIG. 2 shows the structure of the oleyl amide 2,2-dimethylglutarate anion;

the FIG. 3 shows the structure of the oleyl amide benzoate anion;

the FIG. 4 shows the structure of the oleyl amide phenyl acetate anion;

the FIG. 5 shows a route for the synthesis of oleyl ester succinic acid;

the FIG. 6 shows a route for the synthesis of oleyl amide succinic acid;

the FIG. 7 shows a route for the synthesis of oleyl amide succinic acid;

the FIG. 8 compares the viscosity (at a shear rate of 100 s$^{-1}$) of erucyl bis(hydroxyethyl) methyl ammonium chloride (EHAC), oleyl ester succinate (OES), oleyl amide succinate (OAS) and erucyl amide succinate (EAS) viscoelastic gels as a function of temperature;

the FIG. 9 shows the time-dependent viscosity (at a shear rate of 100 s$^{-1}$) of an erucyl amide succinate gel, for various temperatures;

the FIG. 10 compares the stability of oleyl ester succinate, oleyl ester glutarate, erucyl amide succinate, erucyl amide glutarate and erucyl amide maleate gels when aged at various isothermal high temperature conditions;

the FIG. 11 illustrates the dependence of the viscosity of 4 weight percent potassium oleyl amide 2-methylsuccinate in 6% potassium chloride solution as a function of shear rate at various temperatures;

the FIG. 12 illustrates the dependence of the viscosity of 4 weight percent unrefined potassium oleyl amide 2,2-dimethylglutarate in a 6% potassium chloride solution as a function of shear rate at various temperatures;

the FIG. 13 illustrates the dependence of viscosity of a solution of 3 weight percent potassium oleyl amide benzoate and 7 weight percent potassium chloride on shear rate at various temperatures; and the FIG. 14 illustrates the dependence of viscosity of a solution of 4 weight percent potassium oleyl amide phenyl acetate and 4 weight percent potassium chloride on shear rate at various temperatures.

DETAILED DESCRIPTION

The present invention concerns an aqueous fluid for use in the recovery of hydrocarbons such as oil and gas. This aqueous fluid is a wellbore service fluid such as a drilling fluid, a completion fluid, a work over fluid, a packer fluid or a conformance or permeability control fluid and, more particularly, a fracturing fluid.

The fluid of the invention is a viscoelastic gel. Its viscoelasticity may be measured by carrying out dynamic oscillatory rheological measurements as generally described in Barnes H. A. et al., *An Introduction to Rheology*, Elsevier, Amsterdam (1997). In a typical dynamic oscillatory experiment, the fluid is sheared sinusoidally according to the following equation (1):

$$\gamma(t) = \gamma_{(max)} \sin \omega t \qquad (1)$$

where $\gamma(t)$ is the strain, $\gamma(max)$ is the maximum strain, t is time and $\omega$ is the angular frequency. The time-dependent shear stress, $\sigma(t)$, is given by:

$$\sigma(t) = \sigma_{(max)} \sin(\omega t + \delta) \qquad (2)$$

where $\delta$ is the phase angle.

The relative inputs given by the elastic component (G') and viscous component (G") are resolved as follows. Expanding the sine function in equation (2) gives equations (3) and (4) as follows:

$$\sigma(t) = \sigma_{(max)}[\sin \omega t \cos \omega + \cos \omega t \sin \delta] \qquad (3)$$

$$\sigma(t) = \gamma_{(max)}[G' \sin \omega t + G'' \cos \omega t] \qquad (4)$$

where $G' \equiv (\sigma_{(max)}/\gamma_{(max)}) \cos \delta$ and $G'' \equiv (\sigma_{(max)}/\gamma_{(max)}) \sin \delta$.

Equation (4) therefore defines two dynamic moduli: G', the storage modulus or elastic component and G", the loss modulus or viscous component of a fluid having viscoelastic properties.

The terms "viscoelastic gel" as used herein finally mean a composition in which the elastic component (G') is at least as large as the viscous component (G"). In the evolution from a predominantly viscous liquid to a viscoelastic gel, the gel point can be defined by the time when the contribution from the elastic and viscous components becomes equal, i.e. G'=G"; at and beyond this point in time, G'≧G" and the phase angle, $\delta$ is ≧45°.

The fluid of the invention comprises a surfactant. This surfactant is said to be viscoelastic because, unlike numerous surfactants which typically form Newtonian solutions with a viscosity slightly higher than that of water even at high concentration, it is capable of forming viscoelastic gels even at lower concentrations. This specific rheological behaviour is mainly due to the types of surfactants aggregates that are present in the fluids. In the fluids with low viscosity, the surfactant molecules, present at a sufficient concentration, aggregate in spherical micelles whereas, in viscoelastic fluids, long micelles, which can be described as worm- or rod-like micelles, are present and entangle.

The viscoelastic surfactant is amphiphilic. It comprises a hydrophobic tail group and a hydrophilic head group. The hydrophilic head of the surfactant is charged. It can be charged positively and/or negatively. If it is charged positively, the surfactant is said to be cationic. If it is charged negatively, it is said to be anionic. If it is charged both, positively and negatively, the surfactant is zwitterionic. When the surfactant is cationic, it is associated with a negative counterion which is typically Cl$^-$ or an anionic organic species such as the salicylate anion. When the surfactant is anionic, it is associated with a positive counterion, typically K$^+$ or Na$^+$ and, when it is zwitterionic, it is associated with both negative and positive counterions, typically Cl$^-$ and Na$^+$ or K$^+$.

The formulae of the viscoelastic surfactant of the present invention is as follows:

R—X—Y-Z where R is the hydrophobic tail of the surfactant, Z is the charged hydrophilic head of the surfactant, X is a stabilising group and Y is a linear, saturated or unsaturated, hydrocarbon chain of 1, 2 or 3 carbon atoms or a branched, saturated or unsaturated hydrocarbon chain wherein the main chain is of 1, 2 or 3 carbon atoms, possibly incorporating an aromatic ring.

Possibly, the surfactant of the invention is dimeric or oligomeric. In such case, the formula of the surfactant is [R—X—Y-Z]$_n$ where is 2, . . . , N. N is preferably 2 or 3. Practically, the dimeric or oligomeric surfactant comprises a chemical bond linking their hydrophobic tail group R together.

Preferably, R is a fully or partially saturated, linear or branched hydrocarbon chain of at least 18 carbon atoms. Hence, the surfactant is capable of forming viscoelastic fluids comprising rod- or worm-like overlapping micelles when the surfactant concentration in the fluid is greater than its overlap concentration. More preferably, R is CH$_3$(CH$_2$)$_7$CH=CH (CH$_2$)$_8$; CH$_3$(CH$_2$)$_7$CH=CH(CH$_2$)$_{12}$; CH$_3$(CH$_2$)$_7$CH=CH (CH$_2$)$_7$; or CH$_3$(CH$_2$)$_7$CH=CH(CH$_2$)$_{11}$.

X is preferably a cleavable bond which can be broken under downhole conditions of temperature and/or pH. Preferably, X is an ester, amide, reverse ester or reverse amide group. These groups comprise each a chemical function carbonyl. This function is strongly electron-withdrawing. It is possible that, when the hydrophilic head of the surfactant is charged negatively, the carbonyl group withdraws charges in the hydrophilic head of the surfactant. The repulsive interactions between the hydrophilic head groups of the surfactant molecules arranged in a micellar structure then decrease so that the gel is stabilized. When the hydrophilic head group of the surfactant is charged negatively and the carbonyl is part of an amide group, then hydrogen bonding interactions may also stabilise the micellar structure.

Y is a spacer group, which separates the cleavable group X from the hydrophilic head of the surfactant. It is preferably a saturated or an unsaturated linear hydrocarbon chain of 1, 2 or 3 carbon atoms such as —$CH_2$—, —$CH_2$—$CH_2$—, —$CH_2$—$CH_2$—$CH_2$—, —CH═CH—, or a saturated or an unsaturated branched hydrocarbon chain wherein the main chain comprises 1, 2 or 3 carbon atoms such as —$CH_2$—CH($CH_3$)—, —$CH_2$—C($CH_3$)$_2$—, —CH═C($CH_3$)— or —$CH_2$—$CCH_2$—. It can also comprise an aromatic ring. This aromatic ring is, for example, a benzene ring.

Z may be a carboxylate group $COO^-$ or a sulfonate group —$SO_3^-$. It can also be a group —$N^+R_1R_2R_3$ or $N^+R_1R_2R_3$—$COO^-$ where $R_1$, $R_2$ and $R_3$ are each independently hydrogen or a fully or partially saturated, linear or branched, aliphatic chain of at least one carbon atom, possibly comprising a hydroxyl terminal group.

The spacer group Y of the viscoelastic surfactant of the invention is short. Therefore the stabilizing ester, amide, reverse amide or reverse ester group may influence the charge distribution in the negatively charged hydrophilic head group. Hence, the viscoelasticity persists to temperatures above the usual temperatures of use of viscoelastic surfactants.

Examples of anionic viscoelastic surfactants suitable for the implementation of the invention have the formulae as follows:

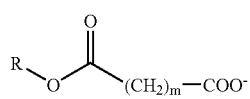

Formula (a)

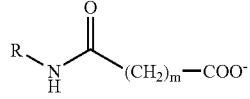

Formula (b)

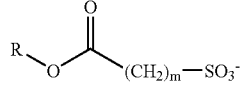

Formula (c)

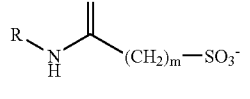

Formula (d)

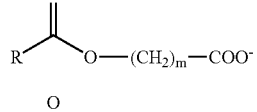

Formula (e)

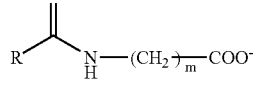

Formula (f)

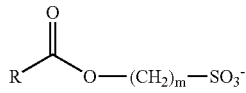

Formula (g)

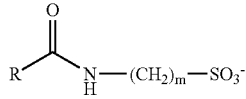

Formula (h)

where R is the hydrophobic tail group of the surfactant as defined above, m is 1, 2 or 3.

The viscoelastic surfactants of the formula (a), (b), (e) and (f) are carboxylates and those of the formula (b), (g) and (h) are sulphonates. The viscoelastic surfactants of the formula (a) and (c) are (reverse) esters, those of the formula (b) and (d) are (reverse) amides, those of the formula (e) and (g) are esters and those of the formula (f) and (h) are amides.

Other examples of anionic viscoelastic surfactants suitable for the implementation of the invention are oleyl amide 2-methylsuccinate anion, oleyl amide 2,2-dimethylglutarate anion, oleyl amide benzoate or oleyl amide phenyl acetic acetate. The formulae of these surfactants are shown, respectively, in the FIGS. 1, 2, 3 and 4.

When, in the formulae R—X—Y-Z as defined above of viscoelastic surfactants of the invention, X is an ester or an amide, then said viscoelastic surfactants are cleavable. As such, they cleave or decompose under downhole conditions to release sub-compounds. The intervening factors in the downhole decomposition of the viscoelastic gels comprising cleavable surfactants are essentially the temperature and the pH. The decomposition of the surfactant molecules leads to a degradation of the viscoelastic gel. However, because of said decomposition, the sub-compounds are not able to form spherical micelles. Therefore, no emulsion is formed and the clean-up of the viscoelastic fluid during hydrocarbons backflow is improved. When surfactant molecules are reverse esters, the sub-compounds released are long chain alcohols. When surfactant molecules are reverse amides, then the sub-compounds are long chain amines. When surfactant molecules are forward esters or amides, then the hydrophobic degradation product is a long chain carboxylic acid. Long chain alcohols, long chain amines and long chain carboxylic acid are breakers of viscoelastic gels. This is the reason why the degradation reaction of viscoelastic gels comprising cleavable surfactants according to the invention can be amplified by their downhole decomposition The viscoelastic surfactant concentration in the aqueous viscoelastic fluid is comprised between about 1 wt % and about 10 wt % and, preferably, between about 1.5 wt % and about 5 wt %. In addition to a viscoelastic surfactant, the aqueous fluid of the invention may comprise salts including, for example, inorganic salts such as ammonium, sodium or potassium chlorides present in concentrations of 1 to 10 wt % and, typically, 3 to 4 wt %, or organic salts such as sodium salicylate. The fluid may also comprise an organic solvent such as isopropanol, which increases the liquefaction of the surfactant molecules.

Practically, all compounds of the fluid of the invention are blended at surface together with the propping agent, which can be, for example, a 20-40 mesh sand, bauxite or glass beads. When subjected to a very high shear rate, the viscosity of the fluid is sufficiently low to allow its pumping downhole. There, the pumped fluid is injected into the formation rocks to be fractured under a high pressure. At that time, the fluid of the invention is sufficiently viscous for carrying the propping agent through the fracture. At a given time after fracturing per se, practically, 4 or 5 hours after injection under pressure of the fluid, the gel degrades. If the viscoelastic surfactant is cleavable, this degradation is amplified by the release of sub-compounds which acts as breakers of the gel. The clean-up of the fracture is thus facilitated.

EXAMPLE 1

Synthesis of Ester Carboxylates

Oleyl ester succinic acid was synthesised using the following procedure. To a solution comprising 50 g of oleyl alcohol in 50 ml of tetrahydrofurane (THF) was added 22 g, that is to say 1.2 mole equivalent, of succinic anhydride. The solution was then refluxed at a temperature of 68° C. for 48 hours to ensure the complete reaction shown in the FIG. 5. THF was then removed under vacuum and 50 ml of petroleum ether was added. The excess of succinic anhydride not soluble in petroleum ether was removed by filtration on Whatman paper 43. The petroleum ether solution was then cooled down and maintained at −10° C. overnight using a refrigerated centrifuge. A white solid was finally collected by centrifuging for 30 min at 9000 rpm. This solid was washed with cold petroleum ether and dried under vacuum. The crude product finally obtained was re-crystallised to remove any impurities to yield a white solid.

An equivalent procedure was used to synthesise oleyl ester maleic acid from maleic anhydride and oleyl ester glutaric acid from glutaric anhydride.

Also, an equivalent procedure was used to synthesise erucyl ester succinic, maleic and glutaric acids from erucyl alcohol.

EXAMPLE 2

Synthesis of Amide Carboxylates

Oleyl amide succinic acid was synthesised using the following procedure. To a solution of 50 of oleyl amine in 100 ml THF was added 22 g, that is to say 1.2 mole equivalents, of succinic anhydride. The solution was then refluxed at a temperature of 68° C. for 48 hours to ensure the complete reaction shown in the FIG. 6. THF was removed under vacuum and 50 ml of petroleum ether was added. The excess succinic anhydride not soluble in petroleum ether was removed by filtration on Whatman paper 43. The petroleum ether solution was cooled down and maintained at −10° C. overnight using a refrigerated centrifuge. The white solid was then collected by centrifuging for 30 min at 9000 rpm. The product was washed with cold petroleum ether and dried under vacuum.

An equivalent procedure was used to prepare oleyl amide maleic acid form maleic acid and oleyl amide glutaric acid from glutaric anhydride.

EXAMPLE 3

Synthesis of Amide Carboxylates

The reagent erucyl acid chloride was prepared from erucic acid in the following manner. To 50 g erucic acid in 20 ml of THF was added 50 ml of thionyl chloride. The reaction was continued under reflux for 30 min and the solvent was removed under vacuum. A light brown liquid, the erucyl acid chloride product, was collected. To this liquid was added a solution/suspension of the sodium salt of beta-alanine in THF. The reaction shown in the FIG. 7 then took place under reflux for 24 hours. The solvent was removed under vacuum and petroleum ether was added. The solution was filtered on Whatman paper 43 and the filtrate solution was then cooled down to −10° C. A light yellow solid product was collected.

EXAMPLE 4

Resistance of Erucyl Amide Succinate and Erucyl Amide Glutarate to High Temperatures On FIG. 9 is plotted the viscosity, at a shear rate of $100\ s^{-1}$, of an aqueous viscoelastic fluid according to the invention comprising 4 wt % of erucyl amide succinate and 4 wt % KCl, at a pH equal to 12, as a function of time, for the following temperatures: 130° C., 150° C., 170° C. and 180° C. A horizontal doted line is positioned at 50 cP on FIG. 9. It defines the limit at which the gel is considered to be insufficient for fracturing applications.

At 180° C., the gel breaks in less than 1 hour. At 170° C., the gel breaks in about 2 hours. At 150° C. however, the viscosity of the gel breaks in about 4-6 hours to reach a viscosity of about 2 cP at about 15 hours. Finally, at 130° C., the viscosity decreases slowly and is still in excess of 50 cP after 5 hours. After 25 hours, the viscosity is still greater than 20 cP.

As a consequence, a fluid comprising erucyl amide succinate may be used notably for fracturing applications between about 260° F. and about 360° F. Under 260° F., it will not degrade significantly and, above 360° F., it may degrade too rapidly to permit the transport of the propping agent and to prevent the fracture from closing. However, it is noted that when applied in a reservoir in which the temperature is 360° F., the fluid will take some time to be treated from surface to reservoir temperature such that its degradation time may be sufficiently prolonged for the application.

Other experiments have been made under the same conditions that above with a gel comprising erucyl amide glutarate. These experiments permitted to show that a viscoelastic gel comprising erucyl amide glutarate may be used for fracturing applications above 300° F.

EXAMPLE 5

Comparison of the Rheology of Aqueous Viscolestic Fluids Comprising Erucyl-N,N-bis(2-hydroxyethyl)-N-methyl Ammonium Chloride, Oleyl Ester Succinate, Oleyl Amide Succinate or Erucyl Amide Succinate Over the Temperature On the FIG. 8 is plotted the viscosity, at a high shear rate of $100\ s^{-1}$, of viscoelastic fluids comprising erucyl-N,N-bis(2-hydroxyethyl)-N-methyl ammonium chloride, oleyl ester succinate, oleyl amide succinate and erucyl amide succinate, as a function of temperature. The horizontal line indicates the level at which the gel is considered to be insufficient for fracturing application.

The viscosity of the erucyl-N,N-bis(2-hydroxyethyl)-N-methyl ammonium chloride gel falls at temperature below the required 50 CP at a temperature of about 180° F. (82° C.). The oleyl ester succinate, oleyl amide succinate and erucyl amide succinate gels remain stable to at least 250° F. (121° C.). Amongst those gels, the erucyl amide succinate remains stable at higher temperatures than those of the oleyl ester and oleyl amide succinate gels. Practically, the viscosity of the oleyl ester succinate gel falls below 50 cP at a temperature of about 260° F. (126° C.), the oleyl amide succinate and the erucyl amide succinate gels can be utilised up to temperatures of 290° F. (143° C.) and 350° F. (176° C.), respectively.

EXAMPLE 6

Comparison of the Degradation Rate of Viscoelastic Gels Comprising Oleyl Ester Succinate, Oleyl Ester Glutarate, Erucyl Amide Succinate, Erucyl Amide Glutarate and Erucyl Amide Maleate Aqueous viscoelastic surfactant fluids comprising, either, oleyl ester succinate, oleyl ester glutarate, erucyl amide succinate, erucyl amide glutarate or erucyl amide maleate were prepared. The initial pH of these fluids has been adjusted using potassium hydroxide. For the above fluids, it is equal to, respectively, 9.5, 12, 12, 12 and 12. On the FIG. 10 is plotted the period of time during which the gel is stable as a function of the temperature. A horizontal line highlights the 5 hours period of time in which it is advantageous to have a gel stable for fracturing applications.

It appears that the oleyl ester succinate viscoelastic gel remain stable approximately 3-7 hours between about 175 (79.44° C.) and about 250° F. (121.1° C.). An increase in the fluid initial pH would have slightly displaced the curve obtained for the oleyl ester succinate viscoelastic gel to the left, that is to say the degradation rate would have increased. Therefore, it is estimated that oleyl ester succinate viscoelastic gels of varying alkaline pH remain stable for a suitable period of time (3-7 hours) when aged under isothermal conditions in the temperature range from 120 (48.89° C.) to about 250° F. (121.1° C.).

The oleyl ester glutarate viscoelastic gel is more stable than the oleyl ester succinate gel. At pH 12, it remains stable more than 5 hours between about 175° F. (79° C.) and about 200° F. (93° C.). A reduction in the fluid initial pH would have slightly displaced the curve to the right, that is to say towards a slower degradation and applicability at higher temperatures. Therefore, it is estimated that oleyl ester glutarate viscoelastic gels, again controlled by their initial pH, remain suitably stable more than 5 hours between about 175 (79) and 250° F. (121° C.).

The erucyl amide succinate viscoelastic gel remains stable more than 4-5 hours between about 250° F. (121° C.) and about 300° F. (149° C.). This gel can be used for fracturing applications in this temperature range. However, applications at even 350° F. are possible as the stable gel time is also influenced by the time to heat up the fluid as it moves from surface into the reservoir.

The erucyl amide glutarate viscoelastic gel remains stable for more than 5 hours between about 300° F. (149° C.) and about 350° F. (177° C.). This gel can be used for fracturing applications in this temperature range or even at temperatures in the range 350-400° F.

Surprisingly, the erucyl amide maleate gel, in which Y, in the formulae R-X-Y-Z, is —C=C—, is not stable at high temperature.

Finally, the aqueous viscoelastic surfactant gels comprising oleyl ester succinate, oleyl ester glutarate, erucyl amide succinate and erucyl amide glutarate are all stable, more than 4-5 hours, at high temperatures. Whatever the temperature at of the formation to be treated in the range 120° F. (49° C.) to 350° F. (177° C.), it is possible to use one the above gels. These form a family of fluids that can be used.

EXAMPLE 7

Dependence of the Viscosity of Oleyl Amide 2-Methylsuccinate Anion, Oleyl Amide 2,2-Dimethylglutarate Anion, Oleyl Amide Benzoate or Oleyl Amide Phenyl Acetic Acetate Viscoelastic Gels as a Function of Shear Rate at Various Temperatures FIG. 11 shows a plot of the shear viscosity of a solution of 4 weight percent of the potassium form of the surfactant and 6 weight percent potassium chloride as a function of shear rate at various temperatures. The low temperature viscosity begins to decrease with increasing temperature above about 176° F. (80° C.)

FIG. 12 shows the dependence of the shear viscosity on the shear rate at various temperatures of a solution of 4 weight percent potassium oleyl amide 2,2-dimethylglutarate and 6% potassium chloride. The solution of the surfactant shows a marked decrease in low temperature viscosity above 104° F. (40° C.). Refinement of the surfactant results in a decrease in the temperature dependence of the low shear rate viscosity.

FIG. 13 shows the dependence of the viscosity of a solution of 3 weight percent potassium oleyl amide benzoate and 7 weight percent potassium chloride on shear rate at various temperatures. The viscosity of the surfactant solution at any shear rate is approximately independent of temperatures in excess of 77° F. (25° C.)

FIG. 14 shows the variation of viscosity with shear rate for a solution of 4 weight percent potassium oleyl amide phenyl acetate and 4 weight percent potassium chloride solution at various temperatures. The low shear rate viscosity of the surfactant solution is independent of temperature below 212° F. (100° C.). At higher temperatures the viscosity shows a systematic decrease at all shear rates. This surfactant gel can be use as a practical fracturing fluid at temperatures below 266° F. (130° C.).

The invention claimed is:

1. An aqueous viscoelastic fluid for use in the recovery of hydrocarbons, comprising:

a monomer, a dimer or oligomer of an anionic or cationic viscoelastic surfactant able to form a viscoelastic gel under downhole conditions, said anionic or cationic surfactant comprising a hydrophobic tail and a hydrophilic head, and being of the following formulae:

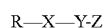

where R is the hydrophobic tail of the surfactant, Z is the hydrophilic head of the surfactant, said hydrophilic head group being charged, X is a stabilising group and Y is a linear, saturated or unsaturated, hydrocarbon chain of 1, 2 or 3 carbon atoms or a branched, saturated or unsaturated hydrocarbon chain wherein the main chain is of 1, 2 or 3 carbon atoms, and wherein:

said anionic or cationic viscoelastic surfactant is cleavable into a subcompound;

said subcompound is a breaker of viscoelastic gels;

said breaker subcompound comprises one of a long chain alcohol, a long chain amine and a long chain carboxylic acid, where the lone chain of the long chain alcohol, the long chain amine and the long chain carboxylic acid comprises 18 or more carbon atoms; and the cleaving of said anionic or cationic viscoelastic surfactant into said breaker subcompound provides for amplification of degradation of the viscoelastic gel formed by said anionic or cationic viscoelastic surfactant.

2. The fluid of claim 1 wherein R is a fully or partially saturated, linear or branched hydrocarbon chain of at least 18 carbon atoms.

3. The fluid of claim 2 wherein R is:
$CH_3(CH_2)_7CH=CH(CH_2)_8$;
$CH_3(CH_2)_7CH=CH(CH_2)_{12}$;
$CH_3(CH_2)_7CH=CH(CH_2)_7$; or
$CH_3(CH_2)_7CH=CH(CH_2)_{11}$.

4. The fluid of claim 1 wherein X is an electron withdrawing group.

5. The fluid of claim 1 wherein X comprises a carbonyl group.

6. The fluid of claim 1 wherein X is an ester, amide, reverse ester or reverse amide group.

7. The fluid of claim 1 wherein Y is:
$-CH_2-$, $-CH_2-CH_2-$, $-CH_2-CH_2-CH_2-$, $-CH=CH-$, $-C_2-CH(CH_3)-$, $-CH_2-C(CH_3)_2-$, $-CH=C(CH_3)-$ or $-CH_2-CCH_2-$.

8. The fluid of claim 1 wherein Y is attached to an aromatic ring.

9. The fluid of claim 1 wherein Z is negatively charged.

10. The fluid of claim 9 wherein Z is $COO^-$.

11. The fluid of claim 1, for use as a fracturing fluid.

12. The fluid of claim 1 for use at a downhole location where the average temperature exceeds 93° C.

13. The fluid of claim 12 wherein the average temperature exceeds 121° C.

* * * * *